US005633724A

United States Patent [19]
King et al.

[11] Patent Number: 5,633,724
[45] Date of Patent: *May 27, 1997

[54] EVANESCENT SCANNING OF BIOCHEMICAL ARRAY

[75] Inventors: David A. King, Palo Alto, Calif.; Jens-Peter Seher, Stuttgart, Germany

[73] Assignee: Hewlett-Packard Company, Palo Alto, Calif.

[*] Notice: The term of this patent shall not extend beyond the expiration date of Pat. No. 5,437,840.

[21] Appl. No.: 520,456

[22] Filed: Aug. 29, 1995

[51] Int. Cl.$^6$ .......................... G01N 21/55; G01N 21/41; G01B 9/02
[52] U.S. Cl. .......................... 356/445; 356/136; 356/352; 422/82.08; 422/82.11
[58] Field of Search .................................. 356/445, 352, 356/136; 422/82.08, 82.11

[56] References Cited

U.S. PATENT DOCUMENTS

| | | | |
|---|---|---|---|
| 4,857,273 | 8/1989 | Stewart | 422/68 |
| 5,038,352 | 8/1991 | Lenth et al. | 372/21 |
| 5,143,854 | 9/1992 | Pirrung | 436/518 |
| 5,437,840 | 8/1995 | King et al. | 356/136 |

FOREIGN PATENT DOCUMENTS

| | | |
|---|---|---|
| WO89/10977 | 11/1989 | European Pat. Off. |
| WO90/05317 | 5/1990 | European Pat. Off. |
| WO91/07087 | 5/1991 | European Pat. Off. |
| WO93/10092 | 6/1992 | European Pat. Off. |
| WO92/10587 | 6/1992 | European Pat. Off. |
| WO92/10588 | 6/1992 | European Pat. Off. |
| 517930A1 | 12/1992 | European Pat. Off. |

OTHER PUBLICATIONS

Anderson, Betty Lise et al., "Use of laser–diode arrays...", Applied Optics, vol. 31, No. 35 (Dec. 10, 1992), pp. 7411–7416.

Bare, H.F. et al., "A Simple Surface–Emitting LED array...", IEEE Photonics Technology Letters, vol. 5, No. 2 (Feb. 1993), pp. 172–175.

Choquette, Steven J. et al., "Planar Waveguide Immunosensor...", Anal. Chem., vol. 64, No. 1 (Jan. 1, 1992), pp. 55–60.

Demtroder, Wolfgang, "Laser Spectroscopy", Springer–Verlag Berlin Heidelberg New York 1982, pp. 390–395.

Fodor, Stephen P.A. et al., "Light–Directed, Spatially Addressable...", Research Article, Science, vol. 251, (Feb. 15, 1991), pp. 767–773.

Godlevski, A.P. et al., "Intracavity Absorption Spectroscopy...", Zhurnal Prikladnoi Spektroskopii, vol. 29, No. 5, Nov. 1978, pp. 1301–1304.

Goldman, Don S. et al., "Miniaturized spectrometer...", Applied Optics, vol. 29, No. 31, (Nov. 1, 1990), pp. 4583–4589.

Harrick, N. J., "Internal Reflection Spectroscopy", Applied Optics, Jan. 1966, pp. 147–177.

Kane, Thomas J. et al., "Monolithic, unidirectional...", Optical Society of America, vol. 10, No. 2 (Feb. 1985), pp. 65–67.

Kooyman, R.P.H. et al., "A fiber–optic fluorescence immunosensor", Dept. of Applied Physics, University of Twente, The Netherlands, The International Society for Optical Engineering.

(List continued on next page.)

Primary Examiner—Frank Gonzalez
Assistant Examiner—Amanda Merlino

[57] ABSTRACT

An apparatus for detecting a target substance in a pixel array is provided. The apparatus has a light source to emit a light suitable for exciting the target substance in the array, a total internal reflection (TIR) member, and a light detector. The TIR member has a TIR surface on which the array is located. The light from the light source passes into the TIR member and is reflected by the TIR surface. The array is within an evanescent field region at the TIR surface. The light detector is adapted to detect light emitted from the array as a result of evanescent excitation of the target substance.

19 Claims, 6 Drawing Sheets

OTHER PUBLICATIONS

Kozlovsky, William J. et al., "Efficient Second Harmonic . . . ", IEEE Journal of Quantum Electronics, vol. 24, No. 6 Jun. 1988, pp. 913–919.

Kronick, M.N. et al., "A New Immunoassay based on Fluorescence . . . ", Journal of Immunological Methods, 8(1975) pp. 235–2310.

Lorrain, P. et al., "Electromagnetic Fields and Waves", W. H. Freeman and Company, 2nd Edition, pp. 504–515.

O'Shannessy, D. J. et al, "Immobilization Chemistries Suitable for Use . . . ", Analytical Biochemistry 205 (1992), pp. 132–136.

Saleh, B.E. et al., "Fundamentals of Photonics", Semiconductor Photon Sources, p. 638.

Sarid, D. et al., "Optical field enhancement . . . ", Applied Optics, vol. 21, No. 22 (Nov. 15, 1982), pp. 3993–3995.

Schiller, S. et al., "Fused–silica monolithic total–internal . . . ", Optic Letters, vol. 17, No. 5 (Mar. 1, 1992), pp. 378–380.

Shiokawa, S. et al., "Interactions of surface plasmons . . . ", J. Appl. Phys., vol. 69, No. 1 (Jan. 1, 1991), pp. 362–366.

Sloper, A.N. et al., "A planar Indium phosphate . . . ", Sensors and Actuators, B1(1990), pp. 589–591.

Soini, E. et al., "Time–Resolved Fluorescence of Lanthanide Probes . . . ", CRC Critical Review in Analytical Chemistry, vol. 18, #2 (1987) pp. 105–154.

EVANESCENT SCANNING OF BIOCHEMICAL ARRAY

FIELD OF THE INVENTION

This invention is related to polymer sequencing and recognition. More specifically, this invention is related to devices and methods for scanning large biochemical arrays.

BACKGROUND

Recently, biomolecular arrays have been successfully created. For example, Fodor, et al., "Light-directed, Spatially Addressable Parallel Chemical Synthesis," *Science*, Vol. 251,767–773 (1991) disclose high density arrays formed by light-directed synthesis. The array was used for antibody recognition. Biomolecular arrays are also described by E. Southern (PCT Publication WO 89/10977) for analyzing polynucleotide sequences. Such biomolecular arrays lend themselves to a large number of applications, from DNA and protein sequencing to DNA fingerprinting and disease diagnosis.

Large scale polymer arrays may be needed for specific applications. In the analysis of large polymeric molecules such as the sequencing of DNA and protein identification, because of the large number of possible combinations, the ability to "read" (i.e., detect differences in) the polymer array is important for such analyses and sequencing to be practicable. For example, in DNA sequencing, one may wish to scan an array of all possible 65,000 8-mers (a 8-mer is a single strand polynucleotide having 8 nucleic bases). Each pixel corresponds to a single 8-mer and practical limits on the amount of optical power required to read this pixel are between 1 mW and 10 mW.

One approach for synthesizing a polymer array on an optical substrate is described by Fodor et at. (1991) supra; PCT publications WO 91/07087, WO 92/10587, and WO 92/10588; and U.S. Pat. No. 5,143,854. Because the apparatus and method of synthesizing a polymer array can be applied in the present invention, these disclosures are incorporated by reference herein. In this approach, an array of different receptors is synthesized onto a substrate using photolithographic techniques. Ligands are washed over the array. Either the ligand is fluorescently labeled or an additional fluorescently labeled receptor is also washed over the array. The result is that fluorophores are immobilized on those pixels where binding has occurred between the ligand and the receptor(s). The array is illuminated with radiation that excites the fluorophores. The pattern of bright and dark pixels is recorded. Information about the ligand is obtained by comparing this bright-dark pattern with known patterns of surface bound receptors. The aforementioned references describe a method for reading the array for the presence of fluorophores. For example, PCT publication WO 92/10587 discloses optically scanning an array by directing excitation with light through a microscope objective and collecting fluorescence through the same objective. All the embodiments described in the PCT Publication WO 92/10587 refer to similar direct illumination of the array. Similarly, PCT Publication WO 92/10092 discloses directly illuminating the array surface in all its embodiments.

While direct illumination of the array is simple, there are some significant disadvantages. For example, excitation radiation reflected from the array surface can enter the fluorescence-collection optics. This reflected radiation can be much brighter than the generated fluorescence. Direct illumination almost always results in excitation and scattering from a large number of molecules other than the fluorophores, additionally creating a possibly larger background signal. This is particularly problematic if the illuminating light passes through a solution in contact with the array. While there may be techniques to reduce these effects (such as temporal, spectral or spatial filtering of the light), their utility is often limited by trade-offs that occur between signal-to-noise and collection time.

Optical-frequency evanescent probing has been investigated for chemical assay. Evanescent surface probing techniques using fluorescence include total internal reflection on prisms (M. L. Kronick and W. A. Little, "A new immunoassay based on fluorescence excitation by internal reflection spectroscopy," *J. Immunological Meth.*, Vol. 8, 235, 1975), waveguides (A. N. Sloper, J. K. Deacon, and M. T. Flanagan, "A planar indium phosphate monomode waveguide evanescent field immunosensor," *Sensors and Actuators*, Vol. B1, 589, 1990), and optical fibers (R. P. H. Kooyman, H. E. be Bruijn, and J. Greve, "A fiber-optic fluorescence immunosensor," *Proc. Soc. Photo.-Opt. Instrum. Eng.*, Vol. 798, 290, 1987); and surface plasmon resonance (J. P. Seher, "Method and apparatus for detecting the presence and/or concentration of biomolecules, "European Patent No. 0 517 930 A1, 1992).

In such evanescent probing techniques, high contrast is achieved against reflected and scattered excitation radiation because the excitation energy does not travel through space but is trapped in a very thin region above the surface. Additionally, the 1/e depth (i.e., the depth for the attenuation of light to 1/e of the original value) of this region may be controlled (P. Lorrain and D. Corson, *Electromagnetic Fields and Waves*, W. H. Freeman, San Francisco, 1970, pp. 520–525).

Evanescent excitation is very different from direct excitation or direct illumination as described in PCT publications WO 92/10587 and WO 92/10092. Gratings are often used to convert direct illumination into evanescent excitation (D. S. Goldman, P. L. White, and N. C. Anheier, "Miniaturized spectrometer employing planar waveguides and grating couplers for chemical analysis, "*Appl. Opt.*, Vol. 29, 4583–4589, 1990). It is well known in the art that gratings may also be generated by acoustic and optical waves and have been used to create evanescent excitation (X. Sun, S. Shiokawa, and Y. Matsui, "Interactions of surface plasmons with surface acoustic waves and the study of the properties of Ag films," *J. Appl. Phys.*, Vol. 69, 362, 1991). However, the prior art methods as illustrated in the above publications for scanning arrays typically employ argon ion lasers, which tend to be expensive and large.

To effectively illuminate a large array requires a large amount of energy. For example, illuminating simultaneously all the pixels in the aforementioned array of 65,000 8-mers requires between 65 W and 650 W. Because of the inefficiency in light generation, sources that generate this amount of optical power will consume much more electrical power than these numbers indicate, making cooling necessary. What is needed is an apparatus and a technique that can be used for detecting a polymeric target substance on a polymer array with high contrast against background noise using compact, low power hardware.

SUMMARY

The present invention provides an apparatus for analyzing a target substance on a pixel array, particularly an array of pixels containing chemicals such as polymers (polymer array). In the present invention, the use of evanescent excitation facilitates the simultaneous illumination of the entire array while minimizing background scattered light.

Further, in accordance with an aspect of the present invention, placing the array (with the substrate, on which the array is supported) inside a high-gain optical cavity (i.e, resonance cavity) affords a significant advantage of evanescent excitation. The optical output from an inexpensive, miniature, and structurally simple (such as solid-state) light source can be trapped inside the optical cavity and can thereby amplify the light intensity a thousand-fold as described by King, et at. (U.S. Pat. No. 5,432,610). If a total internal reflection (TIR) element is placed inside the cavity (as in a preferred embodiment) the intense intracavity radiation can be used to excite evanescently an array on a substrate surface. In such intracavity applications evanescent rather than direct excitation of the surface is preferably used so that the intracavity element has a low optical loss, thereby preserving the large cavity gain. In this embodiment, evanescent excitation permits simple direct fluorescence collection. The advantage of this embodiment can be appreciated by considering the light source required to directly and simultaneously illuminate 65,000 pixels with individual light sources of 1 mW to 10 mW. Because of the requirement for cooling, light sources (e.g., diode lasers similar to SDL-3200 series from SDL, Inc., San Jose, Calif.) that can deliver such an amount of power (higher than 65 W to 650 W) are large, extremely expensive, or impractical.

In most prior art work related to arrays, the excitation light is focused to a spot or a line on the array surface and then the array is mechanically translated to illuminate a different set of pixels. Although PCT WO 92/10587 makes reference to broad field illumination with a Charge Coupled Device (CCD) detector and offering a scanning system with no moving parts, this is described as only effective in cases with large amounts of fluorescence and therefore is not practical in many applications.

As previously mentioned, in the present invention, we combine an array detector with broad field evanescent excitation. Evanescent excitation will result in an increase in signal to noise ratio. This invention can use light efficiently so that no moving part is needed to illuminate or translate the array. An array detector will eliminate the need for all moving parts. An instrument that has no moving parts offers advantages in manufacturability and a longer lifetime. For low level fluorescence applications, the array is excited using intracavity evanescent radiation.

In the present invention, an optical signal may be distinguished from an excitation signal by frequency or time or both. Most widely employed fluorescent dyes, such as rhodamine, have a very fast fluorescent decay time, with the result that simple fluorescence is a frequency shift of the excitation radiation. Nonlinear-optical surface processes, having the advantages of affording larger frequency shifts, can also be used. If a pulsed light source is employed, the technique of time-resolved fluorescence combining shifts in both time and frequency with significant improvements in signal-to-noise is also practicable (E. Soini and T. Lovgren, "Time-resolved fluorescence of lanthanide probes and applications in biotechnology," Crit. Rev. Anal. Chem., Vol. 18(2), 105–154 (1987)). Any of these techniques will be suitable for generating an optical signal in response to evanescent (or direct) excitation, and indicating the presence or absence of ligand-receptor binding.

The present invention can be used for chemical detection of microscopic properties (such as fluorescence, phosphorescence, and the like) of a sample or, more specifically, of a target substance (chemical) contained within the sample. Examples of target substances that the invention is exceptionally well suited to detect include, for example, antibodies, drugs, polynucleotides, cell membrane receptors, sugars, nucleic acids, proteins, and even synthetic molecules. The target substance may even be a gas.

BRIEF DESCRIPTION OF THE DRAWING

The following figures, which show the embodiments of the present invention, are included to better illustrate the pixel array-scanning apparatus of the present invention. In these figures, wherein like numerals represent like features in the several views and structures are not shown in scale.

DETAILED DESCRIPTION OF THE INVENTION

This invention provides apparatuses and methods for high-contrast scanning of (or detection of light from) a chemical (e.g., a polymer) array. Evanescent excitation is utilized to generate an optical signal that indicates the presence or absence of binding between ligands and receptors on pixels of the array. As used herein, the term "pixel" refers to an individual member of the array. The binding pattern so produced allows information to be determined about the presence of the ligand.

Any method for generating evanescent excitation on the array substrate may be employed. Examples include, but are not limited to, any form of total internal reflection (TIR) and grating coupling. Several embodiments for scanning a chemical array are described below. The array surface comprises discrete regions or pixels on which chemical reactions have taken place. Each pixel is probed for the presence or absence of a molecular tag in the vicinity of the surface. When excited by an evanescent electromagnetic field, the molecular tags generate an optical signal. The optical signal is detected and the resulting pattern of light and dark pixels may be analyzed by a device (for example, a computer) appropriate for analyzing such patterns.

Detection of Analytes on Chemical Array

Figure 1:
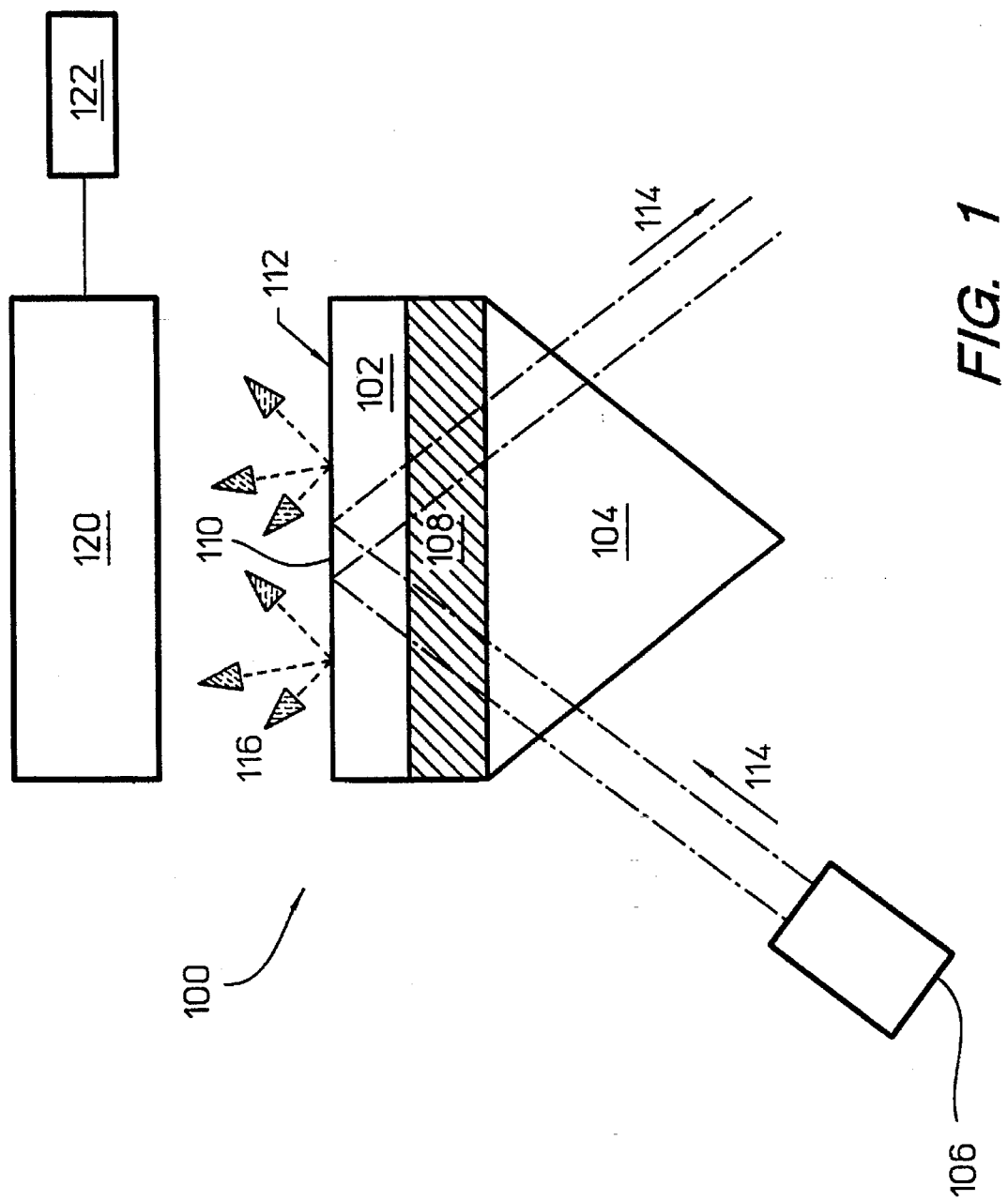
FIG. 1 shows a schematic representation of an embodiment of the present invention for evanescently exciting and detecting fluorescence from a synthesized polymer array using total internal reflection.

FIG. 1 illustrates how evanescent sensing of microscopic properties of analytes (or target substances) is done on a polymer array. Although the application of the present invention is not limited by the method used for binding target substances to form the pixel array, conventional techniques of mounting analytes on an array on a suitable substrate and labeling with molecular tags (such as fluorophores), such as those techniques described in the aforementioned references, can be used. Generally, in such an array, different pixels have different chemicals (such as polymeric segments) suitable for binding to different target substances (or analytes). Thus, by detecting which of the pixels are excited, the presence of a target substance can be determined.

An apparatus 100 is shown in the embodiment of FIG. 1. Substrate 102 is placed in optical contact with prism 104 using an index matching film 108. Substrate 102 and prism 104 are made of optically transparent materials, preferably of the same type. The refractive index matching film 108 may be an oil, but is preferably a compressible optical polymer such as those disclosed by Sjodin, "Optical interface means," PCT publication WO 90/05317, 1990. The prism 104 and the substrate can also be a unitary, integral piece made of the same material (without the refractive index matching film). An array 110 (not drawn separately in the figure as viewing from the side) of molecular tags (which forms the pixel array) is provided on surface 112 of substrate 102. A light beam 114 is provided by a light source 106 and is incident on prism 104 so that total internal reflection occurs on surface 112. In this way, an evanescent electromagnetic field (which will be described in further detail) is created on surface 112. The evanescent electromagnetic field excites the molecular tags (e.g. fluorescence labels) on surface 112, generating an optical signal (e.g. 116). The spatial decay rate and hence the depth of the evanescent field may be controlled by changing the angle of incidence of light beam 114 on surface 112. The angle of incidence is preferably that which maximizes the optical signal 116 from the molecular tags while minimizing any scattered light. The light beam 114 is provided with the correct frequency, temporal, and intensity properties to result in the maximum optical signal from the molecular tags, and in such a way that the evanescent field excites one, some, or all of the pixels of the array.

Suitable light sources include, but are not limited to, lasers, LEDs, coherent frequency-converting devices (an example of which is disclosed by Kozlovsky et at., "Resonator-enhanced frequency doubling in an extended-cavity diode laser," presented at Blue/Green Compact Lasers, New Orleans Feb. 1–5, 1993 and references therein), an array of surface emitting LEDs (Bare et al., "A simple surface-emitting LED array useful for developing free-space optical interconnects," I.E.E.E., Photon. Tech. Lett., Vol. 5, 172–175, 1993), and a suitable array of vertical-cavity surface-emitting lasers (VCSEL) where each polymer array pixel could have its own corresponding laser on the VCSEL array (Salah and Teich, Fundamentals of Photonics, Wiley-Interscience, New York, 1991, p. 638). Examples of molecular tag/light source pairs include CY5/HeNe laser, CY5/laser diode (e.g. Toshiba TOLD9410(s)), CY5/LED (e.g. Hewlett-Packard HMP8150), fluorescein/argon ion laser, and rhodamine/argon ion laser.

The optical signal 116 is collected, imaged, preferably filtered, and detected using optical detection system 120. The selection of the optical detection system 120 for detecting the optical signal 116 is dependent on the application, and a preferred embodiment is described in FIG. 2. A computer, 122, is connected to the detection system 120 for electronically collecting and analyzing the data generated by the detection system.

Complete in situ synthesis of the polymer array could be performed with the apparatus shown in FIG. 1 with the addition of a fluidics systems (not shown) in contact with surface 112. Detection system 120 can be kinematically moved so that UV light from a source can be used to synthesize the polymer array as described in the aforementioned publications. Alternatively, a projection system can be employed to irradiate surface 112 with UV light through prism 104, not requiring movement of system 120.

Figure 2:
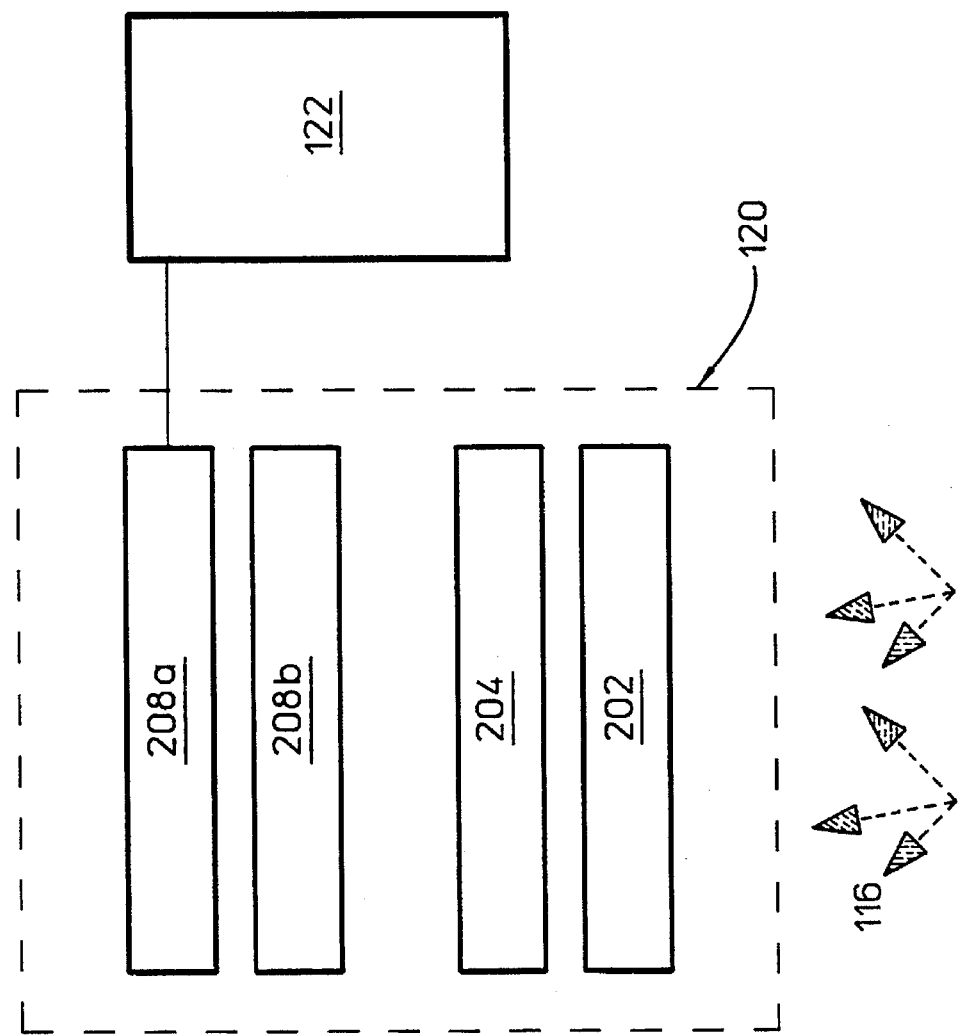
FIG. 2 illustrates a preferred embodiment for detecting optical signal in the present invention.

An example of a suitable detection system 120 is shown in FIG. 2. In this case, light beam 114 (not shown in FIG. 2) is provided so that all the pixels in the array are simultaneously excited by the evanescent field. Here an imaging system 202 collects and images the optical signal 116 through an optical filter 204 and onto a two-dimensional array detector 208a. Imaging systems 202 can contain lenses or a coherent fiber bundle (Hecht and Zajac, Optics, Addison-Wesley, Reading, Mass., 1979, p 136). Filter 204 is chosen to transmit the optical signal and reject radiation at other frequencies. Detector 208a is preferably a two dimensional detector such as CCD array, image intensified CCD, vidicon or video camera. An optional image intensifier 208b, such as Hamamatsu V4170U, can be used in addition to detector 208a if the optical signal 116 is weak. The provided molecular tags preferably generate fluorescent optical signals, but may also generate time-resolved or nonlinear optical signals.

Figure 3:
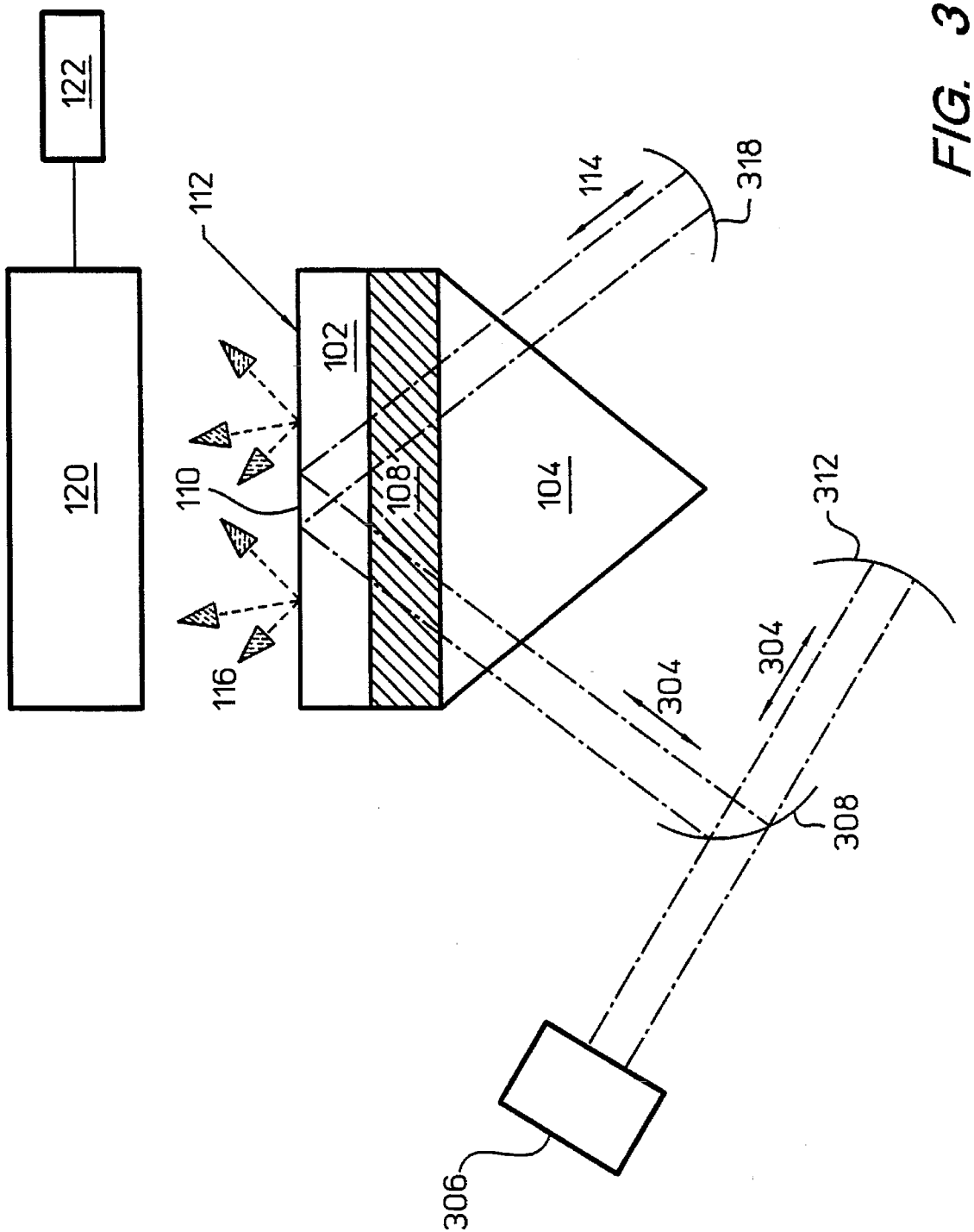
FIG. 3 illustrates an embodiment of the present invention wherein the array is inside a resonance cavity.

As described previously, it is preferred that the polymer array is illuminated by light from within the resonance cavity of an optical resonator. A preferred embodiment is shown in FIG. 3. Here the light beam 114 is replaced by an intracavity beam 304. A light source 306 is used to optically pump an external optical (i.e., resonance) cavity and includes a beam shaping system (not shown). The optical cavity is formed by mirrors 308, 312, 318, and the surface 112. The mirrors 308, 312, and 318 and light source 306 are chosen to optimize the intracavity light beam 304 in a fashion well known to those skilled in the art. The optical cavity may include more or less mirrors than shown in FIG. 3. Light source 306 is preferably a diode laser such as Toshiba TOLD9215 and preferably antireflection coated to enhance the stability of the intracavity beam (King et al., "Diode-pumped power build-up cavity for chemical sensing", U.S. Pat. No. 5,432,610, 1995). In another preferred embodiment, the light source 306 could be placed inside the optical cavity formed by mirrors 308, 312, 318 and surface 112. The light source in this case is preferably a helium neon plasma tube.

Fluorescence is only one of a class of optical probe techniques that rely on light intensity and changes or conversions in the light frequency, and the like, that can be used in the invention. Other examples of linear phenomenon include Raman scattering or surface-enhanced Raman scattering, which are widely used surface sensing techniques. Other non-linear techniques in this class could also be used to advantage. These include second harmonic generation and simulated Raman scattering. Nonlinear optical effects depend on the square or the cube of light intensity and would therefore benefit even more than fluorescence from the increase in intracavity intensity that the invention provides. Such techniques are known in the art.

It is often necessary to partially or completely determine the chemical composition of a sample (e.g., blood glucose level, or sequence of a nucleic acid). The sample contains one or more target substances (analytes) that need to be identified and possibly quantified. The invention performs a suitable assay in the following manner. The sample is pumped across the TIR surface 112, by a fluidics (or gas) handling system (not shown). Each pixel in the chemical array provided by well known techniques on surface 112 contains identical receptor molecules. The receptor molecules may be chosen to specifically bind to one, some, or all of the analytes. The analytes are either fluorescent, fluorescently labeled, or an additional chemical step of fluorescent labeling must be performed. The end result is that certain pixels in the array will have fluorophores chemically bound and others not. The array is illuminated evanescently according to the invention and the resulting checkerboard (i.e., light and dark) fluorescence pattern is detected, and together with knowledge of the receptors yield the desired information about the chemical composition of the sample. The pumps, valves, and syringes that comprise the fluidics (or gas) handling necessary to perform the chemical binding are well known in the art.

Changing the angle of incidence of light at the TIR surface within the resonance cavity changes the 1/e decay depth of the evanescent field. This in turn changes the depth above the TIR surface within which the sample is probed for the presence of the target substance. It is therefore advantageous to optimize the angle of incidence for any particular application of the invention. The choice of optimization method will depend on the intensity of available fluorescence compared with the intensity of the background light. One can measure the intensity during calibration either with the same detector used for actual sensing or with a separate conventional detector. In the simplest case, the fluorescence is much larger than the background light. The angle of incidence is initially set at any angle, and then changed (for example, by rotating the prism) until a maximum intensity is sensed. The angle of incidence is then set at the angle for which the maximum intensity is achieved.

In the more common case, however, the intensity of fluorescence will be much less than the background intensity. In this case, one may use a conventional optical filter in front of the detector (as in FIG. 2), which shows optical filter 204. The optical filter allows the fluorescence to pass, but substantially blocks the background light. Since the filtered background makes up part of the fluorescence signal, to maximize the filtered fluorescence signal while minimizing the unfiltered fluorescence, one can choose an initial angle, measure the filtered and unfiltered intensity, then change the angle and repeat the measurements until an optimum angle is achieved.

The light source, the TIR surface, and if the TIR surface is located in the resonator cavity, the resonator (including the resonance cavity) are selected to provide an adequate evanescent field for illuminating the array. Generally, the power needed to illuminate an individual pixel is about 1 mW to 10 mW. Because in the present invention the light loss is small, such power is available inside the resonance cavity.

If the filtered background intensity is so great that it is still a very large component after filtering, one can use a control section (without a fluorophore) on the TIR surface. In this case, the filter is left in place during the measurement. Fluorescence from the control section and from a section with fluorophore are measured as a function of the angle of incidence. The optimal angle is then chosen to be the angle at which the difference in the signal between the control section and the fluorescence section is a maximum. This calibration method requires a TIR surface with two sections, but this will normally not be a significant disadvantage since the angle of incidence needs to be set only once for any given application.

As previously stated, the present invention can be used to sense the interaction of light in the evanescent field with microscopic properties of the analyte. Preferably, although not necessarily so, the evanescent field is generated by TIR within a resonance cavity. Microscopic properties include interactions of light with single atoms or molecules, such as in fluorescence or phosphorescence. For optical-based transduction methods of microscopic properties such as pixels of a polymer array, the signal (e.g., fluorescence) depends on the intensity of the electromagnetic field. The sensitivity is very often limited by the noise equivalent power of the detector. An increase in intensity reduces the amount of analyte that is necessary to generate the noise equivalent signal, thereby increasing the sensitivity. In simpler terms, the more power the system has available, the less is the amount of the analyte it needs to result in detection. This remains true as the power increases, until saturation or quenching effects begin to occur.

One way to increase power is to use a more intense light source, but this increases electrical power consumption and the physical size of the detector. The preferred embodiment of this invention, however, makes use of the property that the intensity of the electromagnetic field inside the cavity of an optical resonator is often many orders of magnitude larger than the incident light intensity outside the cavity.

Resonance Cavity for Generating Evanescent Field

Figure 4:
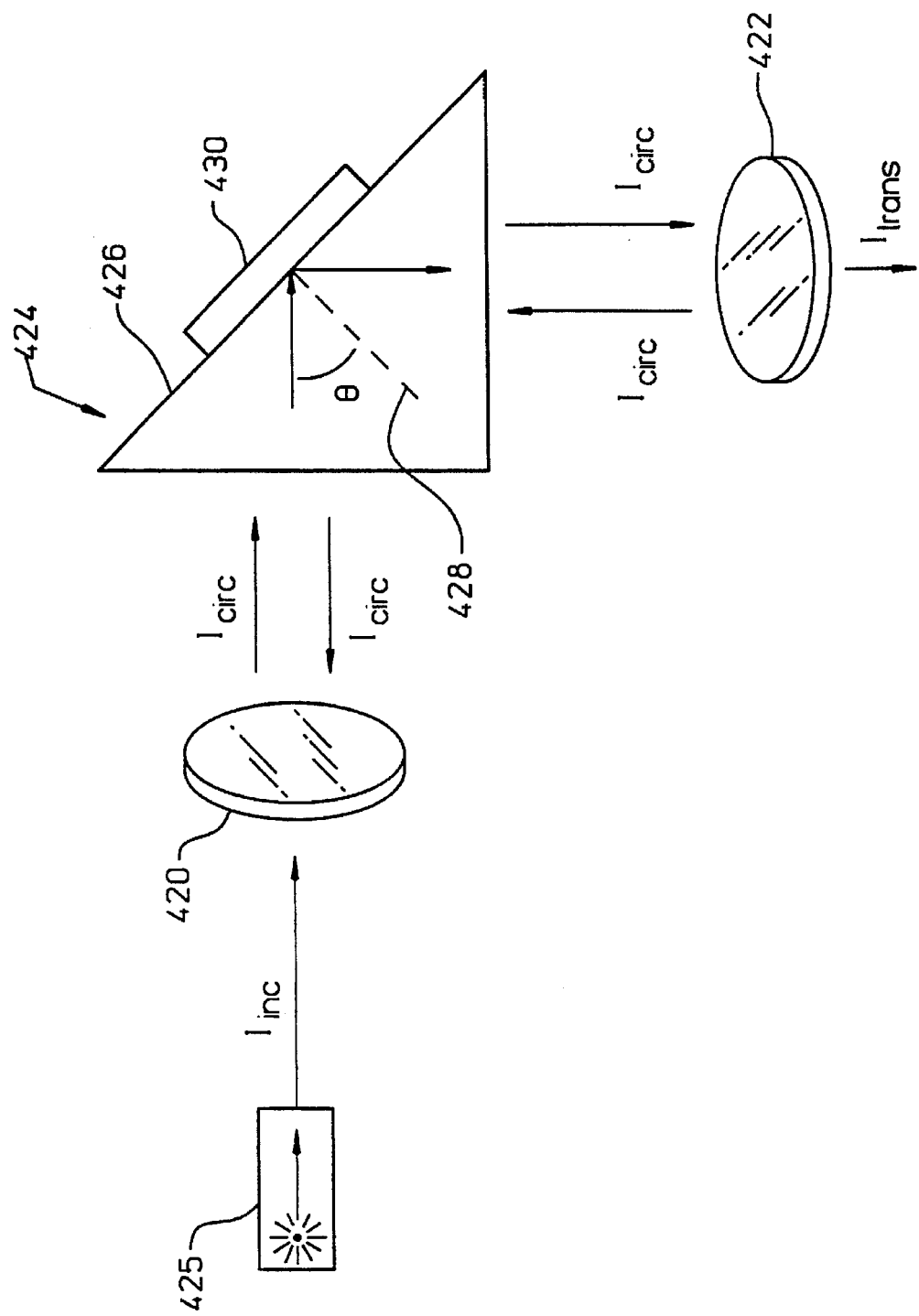
FIG. 4 illustrates schematic representation of a means for evanescently exciting a polymer array using intracavity radiation in a resonance cavity, showing the intracavity light beam.

Although the application of the present invention is not bound by any theory, the following description is presented to facilitate understanding of the invention by one skilled in the art. In the preferred embodiment of the present invention, a TIR surface is located in a resonance cavity (i.e. resonant cavity or optical cavity) to provide an evanescent field for exciting analytes. In this embodiment, light is preferably reflected by the TIR surface substantially without loss. For example, light is reflected by the TIR surface with a loss of about 10 ppm (parts per million) to 1000 ppm of the intensity. An embodiment of such an apparatus (i.e., having TIR surface within a resonance cavity) for analyzing for a target substance on a pixel array of the present invention is depicted in FIG. 4.

As light travels through a medium it may be totally reflected when it strikes an interface with another medium of lower refractive index. This phenomenon is termed total internal reflection (TIR) and occurs for angles of incidence, $\theta$, greater than a critical angle, $\theta_c$. The electromagnetic field then no longer propagates in the second medium but rather exponentially decays away from the interface.

In its simplest form, an optical resonator having a resonance cavity consisting of several mirrored surfaces arranged so that incident light is trapped and bounces back and forth between the mirrors. As an example, consider the case where one of the mirrors is a prism with a face (a TIR surface) that totally reflects the light beam within the resonance cavity (the intracavity beam). At the point of reflection on the prism surface, an evanescent wave is generated with a characteristic decay depth typically of one optical wavelength. Therefore, at the TIR surface, the light is confined to the surface and it interacts only with target chemicals within the decay depth of the surface.

An electromagnetic wave is evanescent in a particular direction when it maintains a constant phase in that direction but has exponentially decreasing amplitude. In the case of TIR, light in the form of an infinite plane wave establishes an exponentially decreasing, evanescent electromagnetic field beyond an infinite, planar TIR surface boundary. Although the electric field has velocity components in the plane of the TIR boundary, there is no velocity component perpendicular to and beyond this boundary. In other words, for the idealized case, only a potential gradient is established beyond a TIR boundary, no energy is actually transported beyond the boundary.

In practical applications, however, neither the incident electromagnetic field nor the TIR surface is infinite. For such a finite configuration, some light diffracts within the boundary (i.e., some energy will flow to just beyond the boundary) and "curves back" toward the boundary, reenters the initial medium, and then exits a small distance away from its entrance point; this is known as the Goos-Hänchen effect. In this invention, this shift is negligible. The large electromagnetic potential gradient beyond the boundary, however, remains.

FIG. 4 is a simplified schematic illustration of a standing-wave optical resonator used according to the invention. In the simplified embodiment of the invention shown in FIG. 4, it is assumed that a light source is located outside of the resonance cavity (although other systems are also practicable). As FIG. 4 shows, the simple optical resonator includes an entrance mirror 420, a reflector mirror 422, and a reflective element 424, which has a TIR surface 426. The mirrors 420, 422 may be either flat or curved and are chosen using conventional criteria to be suitable for generating a stable cavity field, which is well-known in the art. Further, the reflector mirror 422 can also reflect part of the light impinging to generate a stable cavity field and allow part of the light to exit. Suitable, stable cavity fields may also be generated using a configuration with more than two mirrors.

Light is generated by a conventional light source 425, which is preferably an optical gain medium. The light source 425 may be either external to the resonance cavity, as is shown in FIG. 4, or may be incorporated within the cavity. For embodiments of the invention that use an external light source, the light that enters the cavity has an incident intensity $I_{inc}$. In this case, the light source may also include other known optical components (e.g., lens) that enable it to generate a stable cavity field. In all embodiments, the intensity of the circulating field just inside the entrance mirror 420 is $I_{circ}$.

An angle of incidence is defined as the angle θ between the path of light incident on the TIR surface and the normal (indicated by the dotted line 428 perpendicular to the surface 426), to the TIR surface at the point of incidence. For the sake of clarity of explanation and analysis only, the TIR surface 426 is shown as being a plane. This is not necessary to the invention; the definition of angles of incidence for non-planar or piece-wise planar surfaces is well known in the field of optics.

To provide a foundation for determining the sensitivity of the various embodiments of the invention described below, it is useful to determine the intensity of the electromagnetic fields both inside and transmitted by the resonator. Merely for the sake of clarity, the following analysis considers only one TIR surface within the resonance cavity. Those skilled in the art could, however, readily extend the analysis using known mathematical techniques to include many TIR surfaces. This invention is applicable to detection systems with any number of intracavity TIR surfaces.

FIG. 4 shows an embodiment of the invention with a single TIR surface within the resonator cavity. This is similar to the system disclosed in U.S. Pat. No. 5,437,840 (King, et al.), which is incorporated by reference in its entirety herein. In FIG. 4, the TIR reflective element or member 424 is shown as being a prism, so that the TIR surface 426 is one face of the prism. Note that if the reflective element is chosen to be a prism, it is not necessary for it to be a right prism. Moreover, it is not necessary to the invention that the TIR surface be planar. As is pointed out above, the TIR surface may be curved (for example, for certain optical fibers), or piecewise planar or both.

A prism is just one example of a suitable TIR element; other examples include waveguide and fiber, in which cases there may be several TIR surfaces. Additionally, the TIR surface 426 can be on an optically transparent substrate surface such as a glass slide, optical film, or the like, that is optically coupled with the TIR element in a conventional manner, for example, using a compressible optical polymer or refractive index matching oil. The substrate surface may be removable from the TIR element, and may even be disposable. If the test sample (i.e., containing target substances) is attached directly to the TIR element, such as the prism, it may be necessary to clean or replace the prism before testing for another substance, and the alignment of the prism will then have to be checked and possibly readjusted. Providing a removable substrate (e.g. by means of refractive index matching oil on, for example, a prism) eliminates or at least greatly reduces the cost and effort involved in ensuring that the prism is clean and aligned.

To further the analysis with clarity, assume that all electromagnetic fields within the resonator are plane waves. Again, those skilled in the art of optics will readily be able to extend the analysis to embodiments of the invention for which this assumption is not valid. The power reflection coefficient, $R_i$, of the ith mirror (in the general case with I mirrors), is given by $R_i = r_i^2$ (for the two-mirror embodiment shown in FIG. 4, I=1,2) where $r_i$ is the fractional magnitude of the reflective light field of the ith mirror. Now assume that the reflective element 424 (in the illustrated embodiment, a prism), has low-loss entrance and exit faces. The reflection coefficient of the prism is therefore $R_p = |r_p|^2$, and is determined only by the TIR surface 426. According to the invention, an array 430 containing sample(s) to be analyzed is located immediately adjacent to the TIP, surface 426. As is explained below, the sample array is preferably located within about one optical wavelength of the TIR surface.

The optical properties of the sample (on array 430) on the TIR surface 426 are described by the sample refractive index $n_s$. The value of $r_p$ depends on $n_s$, on the refractive index of the prism (or other reflective element), $n_p$, and finally on the angle of incidence, θ. For transverse magnetic (TM) or parallel polarized light, it can be shown (see, for example, Lorrain, P. and Corson, D., *Electromagnetic Fields and Waves*, W. H. Freeman, San Francisco, 1970), that:

$$r_p = \frac{\pm \sqrt{n^2 - \sin^2\theta} - n^2\cos\theta}{\pm \sqrt{n^2 - \sin^2\theta} + n^2\cos\theta} \qquad \text{Eqn. 1}$$

where $n = n_s/n_p$. For sin θ>n (i.e. θ>θ_c, θ being larger than the critical angle θ_c, TIR), $r_p$ is complex, and the negative sign in front of the square root applies. The value of $r_p$ may be expressed more usefully in phasor notation: $r_p = r \cdot e^{j\phi}$. When TIR occurs, r=1, the reflected light has a phase shift φ, and $R_p = 1$.

The power transmission coefficient $T_i$ for the ith of a series of (p) reflective elements is given by $T_i = 1 - R_i, i = 1, 2, \ldots, p$ (in FIG. 4, only one is shown—the prism 424—so that p=1). For a given light intensity, $I_{inc}$ incident on the resonator, the intensity, $I_{circ}$, of the circulating field just inside the entrance mirror 420 (FIG. 4) is determined by the ratio:

$$\frac{I_{circ}}{I_{inc}} = \frac{T_1}{\left| 1 - r_1 r_2 r_p^2 \exp\left(-\alpha L - \frac{j\omega L}{c}\right) \right|^2} \qquad \text{Eqn. 2}$$

where α is the voltage absorption coefficient in the resonator, L is the round-trip path length, and co is the angular frequency of the light. (See, for example, Siegrnan, A.E., *Lasers*, ch. 11, University Science Books, Mill Valley, Calif., 1986.) Eqn. 2 applies strictly only just inside the entrance mirror 420, but for a low-loss standing-wave resonator such as that depicted in FIG. 4, the average intensity is approximately 2 $I_{circ}$ anywhere in the resonator.

Proceeding from equation Eqn. 2, it can easily be shown that if $r_p^2=1$ (that is, simple reflection from a mirror), then $I_{circ}$ will be at a maximum for frequencies $\omega=\omega_m$ that satisfy the equality:

$$\frac{\omega_m L}{c} = 2\pi \cdot m; \quad m = 1, 2 \qquad \text{Eqn. 3}$$

Equation Eqn. 3 defines the resonant mode frequencies, $\omega_m$, of the resonator. These frequencies are separated from one another by a value $2\pi C/L$, which is commonly termed the mode spacing.

Observing that $r_p^2 = r^2 e^{2j\phi}$ and substituting for $r_p$ in Eqn. 2 gives:

$$\frac{I_{circ}}{I_{inc}} = \frac{T_1}{\left|1 - r_1 r_2 r^2 \exp\left(-\alpha L - \frac{j\Omega L}{c}\right)\right|^2} \qquad \text{Eqn. 4}$$

where $\Omega = \omega - (2\phi c)/L$. There may also be a small mount of light, $I_{trans}$ exiting mirror 422.

Throughout the literature, many different structures have been termed resonant (optical) cavities based solely on the fact that they make some use of constructive interference of light waves. A constructive interference alone, however, is not sufficient to create a practical optical transducer with a high sensitivity. The figures in the present disclosure show linear resonators solely for the purpose of illustration. However, even for non-linear resonators (such as a ring resonator), the method of the invention can be done in the same way as for linear resonators: an analyte or sample to be analyzed is placed on an array within the region of the evanescent field of a TIR surface, which is a surface of a reflective element located within the cavity of an optical resonator.

The choice of optical resonator used in a particular application of the invention will depend on the needs and characteristics of that application. In many applications, more complex resonators, such as those described by A. E. Siegman, Lasers, University Science Books, Mill Valley, Calif., 1986, may be more suitable than the simple resonator shown schematically in the figures here. Examples of suitable resonators include Fabry-Perot, "V"-shaped, Michaelson-mirror, Fox-Smith, and Sagnac. The great advantage of these structures is that they generate stable and low-loss optical modes. This means that more of the available light can be utilized for sensing applications. Furthermore, while most useful resonators have Gaussian beam profiles, the analysis used above assumes plane waves. As is mentioned above, however, this assumption is made merely for the sake of clarity and simplicity of illustration and can be extended to non-planar embodiments. In other words, the results one obtains using the assumption of plane waves are essentially the same as for more complicated configurations, but the analysis is greatly simplified.

Using a diode laser as a light source, one could also construct an entirely integrated solid-state transducer suitable for use in the invention. The invention may also incorporate a resonator that is pumped at one wavelength and that generates another wavelength inside the cavity (see, for example, Kozlovsky, W. J., Nabors, C. D. and Byer, R. L., "Efficient second harmonic generation of diode-laser-pumped cw Nd:YAG laser using monolithic MgO:LiNbO$_3$ external resonant cavities," *I.E.E.E.J. Quant. Elec.*, Vol. 24, 913 (1988)); this would make possible the use of a high power source at different wavelengths.

There are many reflective elements with suitable TIR surfaces that could be incorporated within an optical resonator according to the invention. Many of the substrates that can support evanescent optical fields can be utilized for polymer array synthesis. What is important to the present invention is the use of a total internal reflection (TIR) surface on which a chemical array is formed. The TIR surface is part of a TIR element. Examples of optical elements (to provide a substrate) that can support evanescent fields include prisms (for example, Dove prisms), waveguides, fibers, and thin metallic films. Light is confined to travel in a waveguide by TIR. It is well known that channel waveguides can be fabricated by diffusing titanium into a lithium niobate substrate (Salah and Teich, *Fundamentals of Photonics*, Wiley-Interscience, New York, 1991, p. 261). A chemical array may be formed on the exposed surface of the waveguide substrate as outlined above. The cladding from an optical fiber may be removed and a linear array may be deposited. Monolithic resonators could also be fabricated from a single piece of an appropriate material or by coating appropriate mirror surfaces on the end faces of a fiber or waveguide. For example, in fields unrelated to chemical sensing, Kane, T. J. and Byer, R. L., in "Monolithic unidirectional single mode Nd:YAG ring laser," *Opt. Lett.*, Vol. 10, 65 (1985), describe a monolithic nonplanar ring resonator. Similarly, a miniature monolithic ring resonator with a finesse of 5100 is described in the article "Fused-silica monolithic total-internal-reflection resonator," Schiller, S., Yu, I.I., Fejer, M. M., and Byer, R. L., *Opt. Lett.*, Vol. 17, 378 (1992), and in U.S. Pat. No. 5,038,352 (Lenth and Risk, 6 August 1991).

Embodiments of Intensity—Dependent Evanescent Excitation

A few of the preferred embodiments of this invention advantageously makes use of the high intensity of light inside a resonant cavity to elicit evanescent excitation of molecules in an array. This high (increased) intensity can be demonstrated by evaluating Eqn. 2, assuming no intracavity losses ($\alpha=o$), equal mirror reflectivities, $R=R_1=R_2$, $\theta>\theta_c$, (that is, TIR), and that the incident light frequency is tuned to a cavity resonance. For these conditions, Eqn. 2 reduces to $I_{circ}/I_{inc}=1/(1-R)$. Mirrors are readily available (e.g., from Research Electro-Optics, Boulder, Colo.) that have losses as low as 20 ppm (R=0.99998), resulting in a theoretical intracavity amplification factor of $I_{circ}/I_{inc}=1/(1-R) =50,000$. Although other intracavity losses decrease this number, one can easily achieve experimental amplification factors of greater than $10^3$ using the invention and commercially available mirrors.

Figure 5:
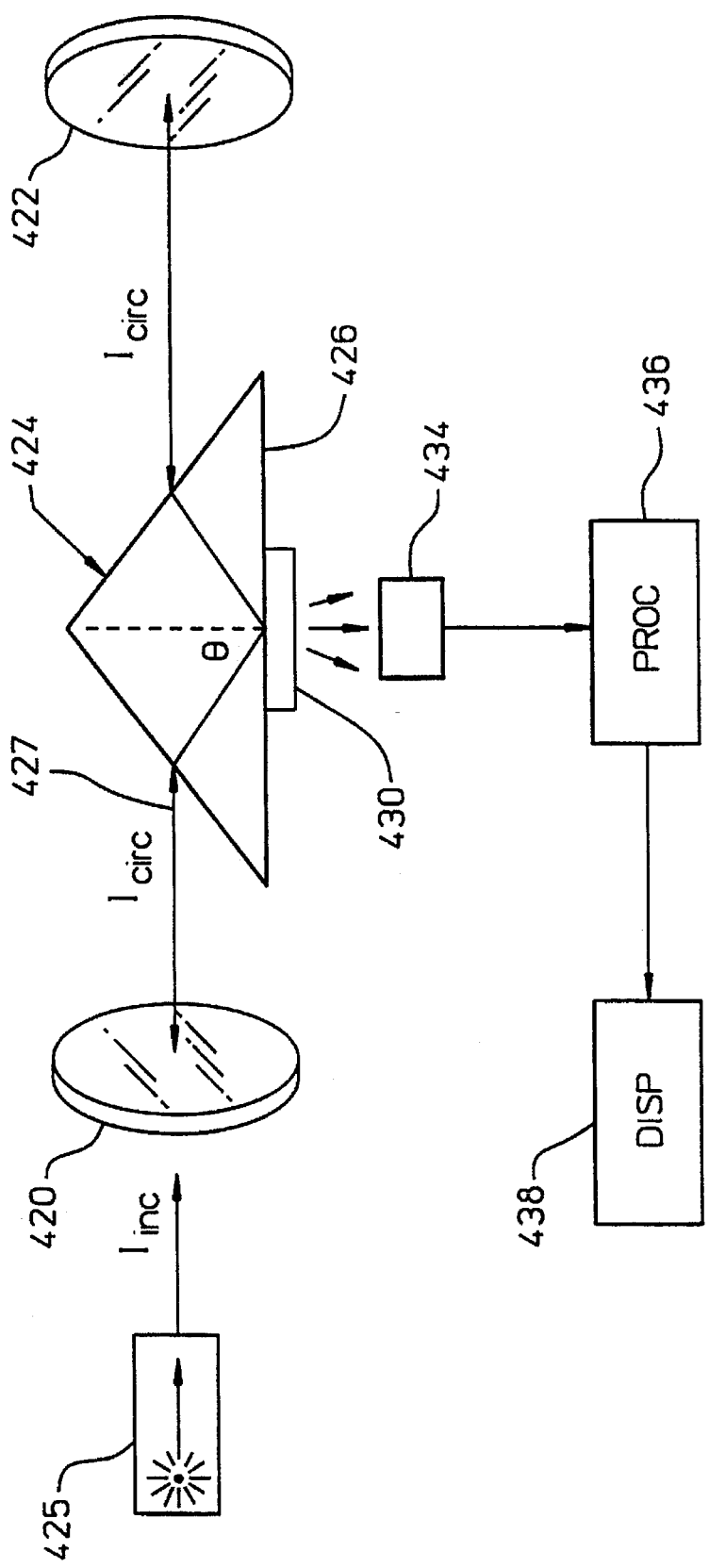
FIG. 5 illustrates a schematic representation showing an alternative embodiment of using intracavity radiation to evanescently excite a chemical array.

FIG. 5 illustrates schematically an embodiment of evanescent excitation in this invention that uses an external light source, having a mirror arrangement different from that of FIG. 4. Features of this embodiment that are functionally the same as those described in FIG. 4 have the same reference numbers in FIG. 5 as they have in FIG. 4. The source 425 is frequency-locked to the resonant frequency of the cavity using techniques that are well known in the art.

Because the invention can, and preferably does, operate with a light source that is external but frequency-locked to the cavity, the light source may be a semiconductor laser such as a diode laser or a superluminescent diode, preferably antireflection-coated. This gives the invention a great advantage over conventional systems in which the laser gain medium is inside the optical resonator (the optical cavity).

Diode lasers and other semiconductor light-generating devices are miniature devices that typically require ten to one hundred times less current than internal gain media and, when coupled to an external resonant optical cavity as in this invention, they can be operated with the same or even higher intracavity power. Systems with an internal gain medium cannot use such compact semiconductor devices as their light source, since these devices typically cannot withstand the strong field that is generated within the cavity. Such systems are thus limited in that they provide no way to employ diode lasers and maintain high sensitivity through large intracavity power. Semiconductor light sources such as diode lasers also permit small optical cavities to be employed. This has the added advantage that the size of the detection system as a whole can also be reduced.

In the illustrated embodiment, a prism is used as the reflective element 424. The prism 424 has a TIR face (or surface) 426 where sensing is performed, and its entrance and exit faces are preferably at Brewster's angle in order to minimize loss. As is discussed above, other members or elements may be used instead of a prism to provide the TIR surface. The two-way light path within the cavity is indicated by line 427, which shows two-way arrows. The target substance i.e., analyte (e.g. on a polymer array) 430 is mounted in any conventional manner at the TIR surface 426 so that it is within the region of the evanescent field of the light reflected by the TIR surface 426. Suitable analyte mounting methods including direct, renewable or non-renewable chemical attachment as in the aforementioned methods can be used.

In the embodiment shown in FIG. 5, the mirror 420 still forms an entrance mirror, since light from the source 425 passes through it into the resonant cavity, but no light is transmitted through the mirror 422. In other embodiments of the invention, the light source 425 can be included between the mirrors 420, 422, in the optical path. Depending on the embodiment, neither, one, or both of the mirrors 420, 422, will partially transmit, or will be partially or wholly reflective.

In this embodiment, it is assumed that the analyte either fluoresces naturally in the presence of electromagnetic excitation, or is provided with a fluorescing tag such as a fluorophore. As is mentioned above, the evanescent intensity $I_{circ}$ is many orders of magnitude larger than the incident intensity $I_{inc}$. Because of this, the degree of electromagnetic excitation within the evanescent field region at the TIR surface will also be many orders of magnitude greater than the degree of excitation that can be obtained from the incident light. The evanescent field will therefore either cause detectable fluorescence in much smaller mounts of analyte than are needed by conventional systems, or will be able to cause equivalent detectable fluorescence using much less source optical power.

Fluorescence from the analyte (from an array 430) is indicated in FIG. 5 by three outward-radiating arrows and is detected by a conventional fluorescence detector 434. The flourescence detector 434 may be any known device that is capable of detecting light from an array and preferably generating electrical output signals that correspond to the intensity of light from fluorescence that strikes its detection surface or elements. The fluorescence detector 434 is preferably connected to a processor 436, which applies known methods to convert the signals from the detector 434 to a form suitable for transmission to another system and/or for display on a conventional display device 438.

According to the invention, the gain medium or source 425 (including other conventional optics), the resonator, and the fluorescence detector 434 may be manufactured into a single, compact monolithic device. Such a device would consume very little electrical power yet would still have a sensitivity that is the same or greater than existing devices. This is particularly advantageous for analyzing polymer arrays because of the large surface occupied by an array. The ability to produce an adequate amount of excitation in the array for detection with little electrical power makes possible a compact monolithic device of the present invention. As previously described, in other embodiments of the invention, waveguides or fibers may be used as the reflective element 424 in place of the prism shown in FIG. 5.

Figure 6:
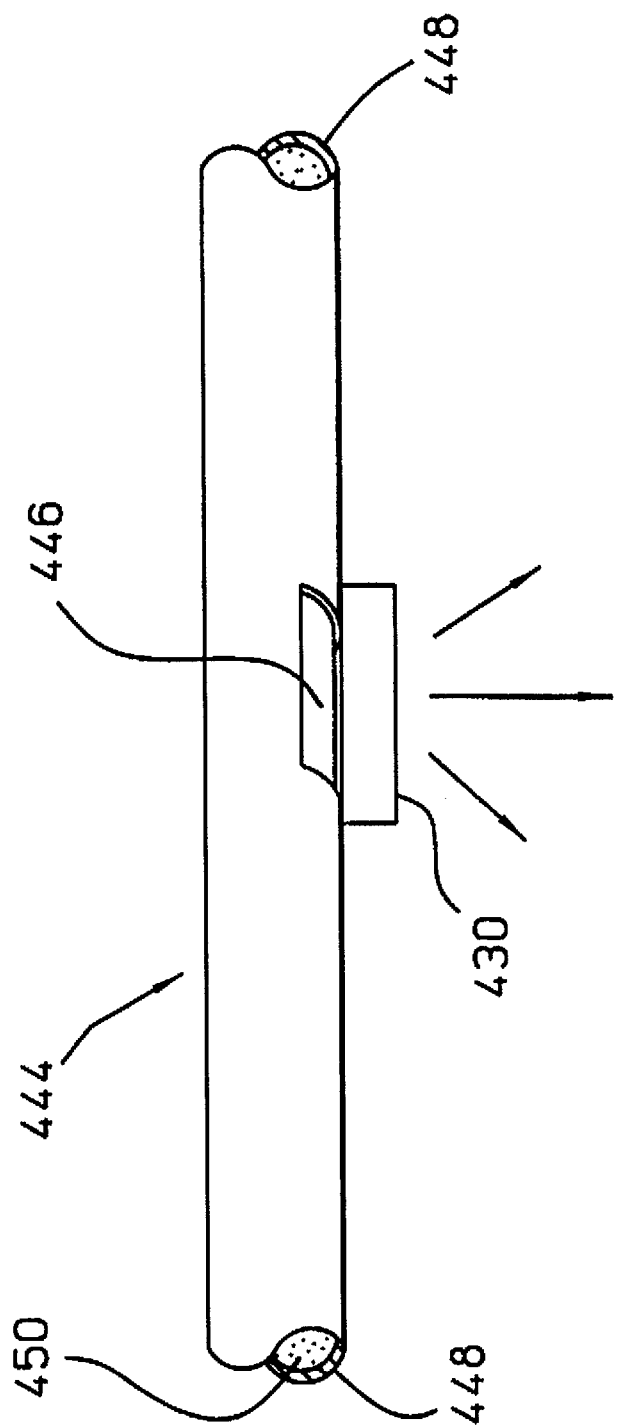
FIG. 6 illustrates an embodiment of the present invention wherein a resonator having a reflective wall (other than the terminal elements) is used.

FIG. 6 illustrates an embodiment of the invention that increases the enhancement factor of the resonator by including a reflective element that also has optical gain ($\alpha<o$). In this embodiment, the resonator comprises a fiber laser 444 (for clarity, only a portion of the fiber of this otherwise known device is illustrated), in which a TIR surface 446 is created by removing a portion of cladding 448 that typically surrounds the actual optical fibers (e.g., fiber 450). The light source, mirrors, and detection and processing circuitry are not shown for the sake of clarity of illustration; these elements may be the same—physically and/or functionally—as those described above for the embodiment shown in FIG. 5.

Since a fiber laser typically has optical gain, the evanescent field in the unclad region forming the TIR surface will be very large. Sensing of fluorescence (in applications using fluorescing analytes), is preferably carried out using detection and processing circuitry as shown and described for FIG. 5 with the analyte in array 430 mounted adjacent to the "window" in the cladding, that is, adjacent to the TIR surface 446. Similarly, waveguides can be used in an analogous manner. Of course, waveguides do not necessarily have a cylindrical shape, as long as there are surfaces withing the waveguide for the propagation of light. A surface on the waveguide can be used as the TIR surface for generating the evanescent field.

According to the invention, as previously mentioned, the source 425 can be placed within the resonance cavity of FIG. 5. In this embodiment, the light source may require different conventional optics, but needed changes will be known to those skilled in the art. A suitable light source for this embodiment would be a helium neon laser tube. Helium neon lasers are commercially available that have circulating powers greater than 100 W, but are still quite compact. A suitable laser tube is manufactured, for example, by Particle Measurement Systems of Boulder, Colo., USA. Other types of lasers may, however, of course be used. Sensing of fluorescence is performed as for the embodiment shown in FIG. 5.

In the embodiments shown in FIGS. 5–6, the great intensity of the intracavity evanescent field is used to excite fluorescence of molecules in a large number of pixels in the vicinity of the TIR surface. Since even trace amounts of the fluorescing analyte can be detected, the fluorescence does not act as a significant loss mechanism for the resonator and the light in the resonator can be maintained at high intensity.

As an example of how the present invention can be applied, consider, the sequencing of DNA with an array of all possible 65,000 8-mers. Each array pixel consists of a unique 8-mer. The methods of Fodor et. al, *supra*, is used for generating this array and for sequencing DNA using fluorescence. The result is each pixel contains a number of fluorophores. A suitable fluorophore is CY5. This array is represented by 430 of FIG. 4. One requires at most about 650 W to optically probe all array pixels simultaneously. This power is achieved using the following components. With reference to FIG. 4: a diode laser, such as Philips CQL806D, which has been anti-reflection coated is used for emitting laser light. Circularizing and focusing lenses match the diode laser output into the optical cavity formed by mirrors 420, 422, and TIR element 424. Mirror 420 has a transmission loss between 1000 ppm and 1 ppm, preferably 200 ppm to 600 ppm. Mirror 422 has a transmission loss between 1000 ppm and 1 ppm, preferably 10 ppm. The spacing of the mirrors 420 and 422 and their curvature is appropriate to form a spot that illuminates the entire array. Suitable spacings are from about 5 cm to 1 m and curvatures are from about flat to 5 cm. The detector (not shown in FIG. 4 but shown as 120 in FIG. 5) may be a commercial CCD of the type supplied by Hammamatsu.

What is claimed is:

1. An apparatus for detecting a target substance in a pixel array comprising:
    (a) a light source to emit a light suitable for exciting the target substance;
    (b) a total internal reflection (TIR) member having a TIR surface on which a pixel array is located, the light from the light source passing into the TIR member and is reflected by the TIR surface, the pixel array being within an evanescent field region at the TIR surface; and
    (c) a light detector for detection of light emitted from the pixel array as a result of evanescent excitation of the target substance.

2. The apparatus of claim 1 further comprising an optical resonator that has a resonance cavity for the light generated by the light source wherein the TIR member is located within the resonance cavity such that light traveling within the resonance cavity impinges on the TIR surface.

3. The apparatus of claim 2 wherein the light source is a gain medium of a laser and is located outside the resonance cavity.

4. The apparatus of claim 2 wherein the light source is an antireflection-coated semiconductor laser.

5. The apparatus of claim 1 wherein the light from the light source is reflected substantially without loss by the TIR surface.

6. The apparatus of claim 1 wherein the light source irradiates all the pixels of the pixel array simultaneously.

7. The apparatus of claim 1 wherein the TIR member is stationary during light detection.

8. The apparatus of claim 1 wherein the light detector is motionless during light detection.

9. The apparatus of claim 1 further comprising a prism and a refractive index match/ng film wherein the refractive index matching film is disposed between the TIR member and the prism such that the light from the light source passes through the prism, the refractive index matching layer and the TIR member before impinging on the TIR surface.

10. The apparatus of claim 1 wherein the light detector is a two dimensional array detector.

11. The apparatus of claim 1 wherein the apparatus further comprises an optical filter and optical fibers for transferring light from the optical filter to the detector.

12. The apparatus of claim 1 wherein pixels in the pixel array are pixels having polymeric sections for coupling with polymeric target substances.

13. A method of analyzing a pixel array of chemical molecules for a target substance, comprising:
    (a) contacting a chemical array with a sample suspected of containing a target substance to form the pixel array;
    (b) directing light from a light source to pass into a total internal reflection (TIR) member having a TIR surface and an array surface on which the pixel array is located to result in an evanescent field region such that the pixel array is within the evanescent field region at the TIR surface, thereby causing excitation of the target substance on the pixel array, the light from the light source being reflected from the TIR surface; and
    (c) detecting light emitted from the pixel array as a result of the excitation of the target substance caused by the evanescent field.

14. The method of claim 13 further comprising mounting the TIR member inside an optical resonator that has a resonance cavity for the light generated by the light source such that light traveling within the resonance cavity impinges on the TIR surface.

15. The method of claim 13 wherein the light from the light source is reflected by the TIR surface substantially without loss.

16. The method of claim 13 wherein the light source irradiates all pixels of the pixel array simultaneously.

17. The method of claim 13 wherein the TIR member is stationary during light detection.

18. The method of claim 13 wherein the light detector is motionless during light detection.

19. A method of making an apparatus for detecting a target substance on a pixel array comprising:
    (a) mounting a total internal reflection (TIR) member on a support, the TIR member having a TIR surface on which the pixel array can be located, the pixel array being capable of binding the target substance;
    (b) mounting a light source on the support to irradiate a light suitable for exciting the target substance on a pixel array located on the TIR surface such that the light from the light source passes into the TIR member and is reflected by the TIR surface to result in an evanescent field region, the pixel array being within the evanescent field region at the TIR surface; and
    (c) mounting a light detector on the support for detecting light emitted from the pixel array as a result of the evanescent excitation of the target substance.

\* \* \* \* \*